United States Patent [19]

Shetty et al.

[11] Patent Number: 4,575,487
[45] Date of Patent: Mar. 11, 1986

[54] METHOD FOR DETERMINATION OF TRANSGLUCOSIDASE

[75] Inventors: Jayarama K. Shetty; J. John Marshall, both of Elkhart, Ind.

[73] Assignee: Miles Laboratories, Inc., Elkhart, Ind.

[21] Appl. No.: 497,797

[22] Filed: May 25, 1983

[51] Int. Cl.$^4$ .............................................. C12Q 1/48
[52] U.S. Cl. ...................................... 435/15; 435/18; 435/184; 435/803
[58] Field of Search ....................... 435/15, 22, 18, 97, 435/184, 193, 803, 814; 436/127

[56] References Cited

U.S. PATENT DOCUMENTS

| | | | |
|---|---|---|---|
| 3,042,584 | 7/1962 | Kool et al. | 195/31 |
| 3,249,514 | 5/1966 | Bode et al. | 435/96 |
| 4,019,960 | 4/1977 | Frommer et al. | 435/803 |
| 4,062,950 | 12/1977 | Frommer et al. | 435/18 |
| 4,109,075 | 8/1978 | Deaton | 536/127 |

OTHER PUBLICATIONS

Benson et al, Journal of Chemical Technology Biotechnology, 1982, vol. 32, pp. 790–798.
The Merck Index, Tenth Edition, 1983, p. 3, item 11.
*J. Jap. Soc. Starch Sci.*, 27, 2, pp. 114–119 (1980).

*Primary Examiner*—Sam Rosen
*Assistant Examiner*—William J. Herald
*Attorney, Agent, or Firm*—Jerome L. Jeffers

[57] ABSTRACT

Disclosed is a method for the determination of transglucosidase activity in glucoamylase preparations suspected of having TG activity. The method involves inhibiting the glucoamylase in the preparation with acarbose and then measuring the uninhibited TG activity by conventional means.

5 Claims, 1 Drawing Figure

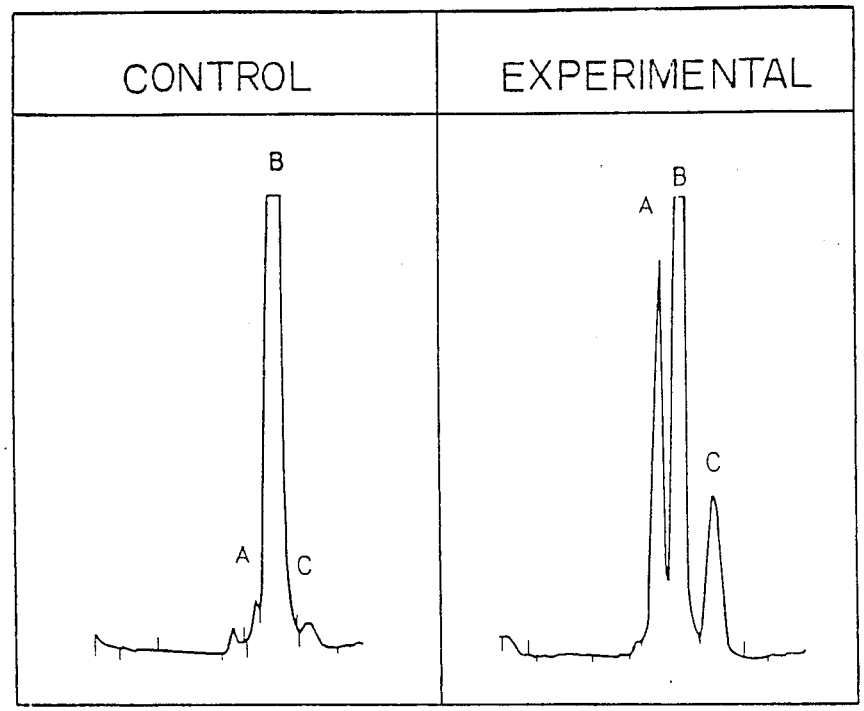
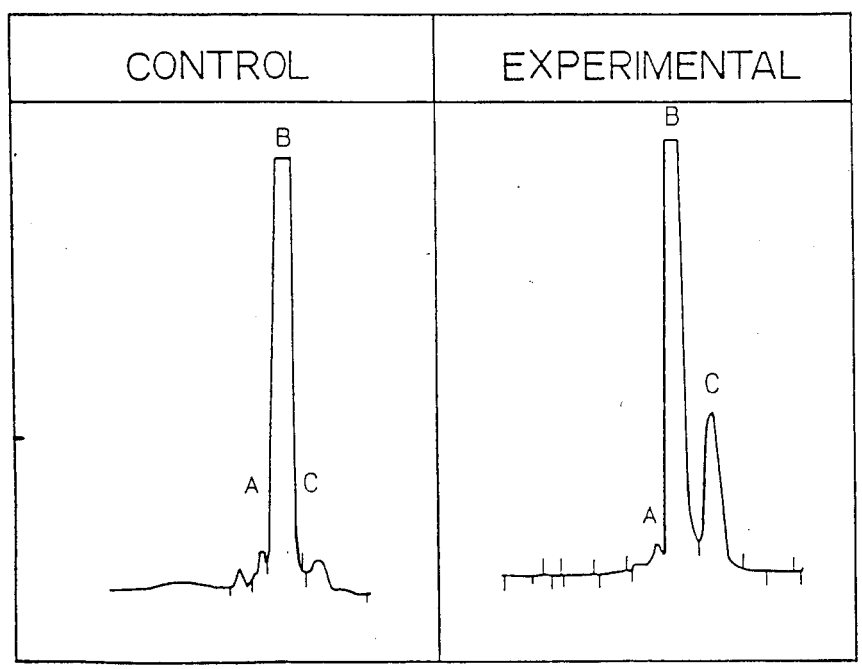

METHOD FOR DETERMINATION OF TRANSGLUCOSIDASE

BACKGROUND OF THE INVENTION

The commerical production of crystalline D-glucose and high glucose syrups from starch is generally carried out by an enzymatic process using glucoamylase of fungal origin, particularly enzyme preparations derived from fungi of the Aspergillus and Rhizopus genera. A preferred method of producing this enzyme involves the fermentation in an appropriate nutrient medium of an organism from the species *A. niger*. Glucoamylase hydrolyzes both $\alpha$-D-($1\rightarrow4$) and $\alpha$-D-($1\rightarrow6$) glucosidic bonds of starch. Hydrolysis by glucoamylase of $\alpha$-D-($1\rightarrow4$) bonds occurs substantially faster than the rate of hydrolysis of $\alpha$-D-($1\rightarrow6$) bonds. It has been known for many years that the culture filtrate from *A. niger* fermentations contain a second enzyme, transglucosidase (TG) which is capable of transferring glucosyl residues from sugars containing $\alpha$-D-($1\rightarrow4$) or $\alpha$-D-($1\rightarrow6$) glucosidic linkages to the 6-position of other sugar molecules. The formation of $\alpha$-D-($1\rightarrow6$) linkages causes a marked decrease in the glucose yield during the enzymatic conversion of starch.

Because of the reduction in glucose yield caused by the presence of transglucosidase in glucoamylase preparations, techniques have been developed to remove this contaminant. One technique is disclosed in U.S. Pat. No. 3,042,584 in which a fungal amylase preparation containing transglucosidase and glucoamylase activities is contacted with a clay mineral. This procedure results in selective adsorption of transglucosidase by the clay thereby facilitating separation of the enzymes by liquid/solid separatory techniques.

Before any such separation of enzymes is attempted and for quality control of finished glucoamylase product, it is essential to be able to determine the level of transglucosidase in the glucoamylase preparation that is to be or has been treated. One method for the determination of transglucosidase activity is disclosed in the aforementioned '584 patent. This method is based on the conversion of maltose into glucose by the glucoamylase preparation under test. The extent of conversion is determined by comparing the optical rotation of the product produced by the glucoamylase preparation under test with that produced by a standard (TG-free) glucoamylase preparation. The presence of TG results in a product with higher specific rotation than that produced under identical conditions by glucoamylase free of TG. This method suffers from the disadvantage of being slow (requiring 72 hours to complete) and it is not quantitative because the two enzymes (glucoamylase and transglucosidase) compete for the same substrate (maltose).

It would be desirable, and it is an object of the present invention, to provide a quantitative, rapid method for the determination of transglucosidase activity, particularly one that can be used for measurement of TG activity in enzyme preparations containing both glucoamylase and transglucosidase activity.

SUMMARY OF THE INVENTION

The present invention is a method for the quantitative determination of transglucosidase activity in glucoamylase preparations which method comprises the steps of:

(a) providing a culture filtrate of a glucoamylase preparations suspected of having transglucosidase activity;

(b) adding a quantity of a selctive inhibitor to the culture filtrate sufficient to inhibit the glucoamylase activity without inhibiting the transglucosidase activity;

(c) introducing a substrate susceptible to transglucosidase activity to the culture filtrate so treated; and (d) determining the transglucosidase activity by measuring the production of one specific product produced by the action of transglucosidase on the selected substrate as a function of time.

DESCRIPTION OF THE INVENTION

A particularly effective, selective inhibitor is acarbose which is identified by *J. Jap. Soc. Starch Sci.*, 27, pages 114–119 (1980) as BAYg 5421 and shown to be an inhibitor of amylolytic enzymes. The difference in the effect of acarbose on glucoamylase and transglucosidase has led to the development of a sensitive assay for transglucosidase in the presence of glucoamylase. To determine the level of acarbose needed to inhibit glucoamylase completely, purified glucoamylase equivalent to one DU (the amount that liberates one gram of reducing sugar per hour under the conditions of the assay published in U.S. Pat. No. 3,249,514) is treated with graded amounts of acarbose and the remaining activity measured by incubation with maltose under appropriate conditions, for example, at pH 4.2 and 37° C. with a maltose concentration of 10%. The extent of inhibition of glucoamylase activity is increased with increasing concentrations of acarbose up to 50 $\mu$g acarbose per DU enzyme and above, such concentrations causing 100% inhibition. In order to determine the effect of acarbose on TG activity, glucoamylase (one DU) containing TG (40 TG units, vide infra) was treated with different concentrations of acarbose and then incubated with maltose (10%), at pH 4.8, and 37° C. for one hour. The enzyme reaction was then terminated by heating the reaction mixture in a boiling water bath for 15 minutes and transglucosidase activity was determined by measuring, using liquid chromatography, the amount of panose produced during the reaction period. In these experiments, it was observed that the amount of panose produced increased with increasing levels of acarbose up to 50 $\mu$g per DU of glucoamylase and, thereafter, remained constant up to 500 $\mu$g of acarbose per DU of glucoamylase. However, further increase in the acarbose concentration was found to cause a steady decrease in the amount of panose produced, indicating inhibition of TG at concentrations of acarbose exceeding 500 $\mu$g/DU glucoamylase. In these experiments, panose was routinely measured by a high pressure liquid chromatography procedure which separated this compound from glucose and maltose. Alternative procedures for specific determination of panose can be used equally well. The results of the experiments described are set out in table I.

From table I, it can be determined that under the conditions of this experiment there is a wide range of acarbose concentrations (50–500 $\mu$g/DU) at which glucoamylase activity is completely inhibited without there being any inhibition of transglucosidase activity. Therefore, by introducing 50–500 $\mu$g acarbose per DU to the glucoamylase preparation, it is possible to inhibit glucoamylase activity completely without affecting the TG activity.

It is recognized that the inhibition of glucoamylase or acarbose and the measurement of transglucosidase activity may equally well be conducted under different conditions. In order to work at such alternative conditions, it is necessary to determine the effect of a range of acarbose concentrations under the conditions selected, and in this way to identify a level of acarbose sufficient to give complete inhibition of glucoamylase without inhibiting transglucosidase activity.

Likewise, since transglucosidase acts on other substrates besides maltose, including but not limited to members of the malto-oligosaccharide series higher than maltose, it is not mandatory that maltose be used as substrate. Maltose is a preferred substrate because of the fast rate of reaction and relative lack of complexity of the products obtained by action of TG upon it, whereas, other substrates often tend to yield a multiplicity of products and the specific determination of the primary reaction product is likely to be more difficult.

TABLE I
EFFECT OF ACARBOSE ON GLUCOAMYLASE ACTIVITY AND TRANSGLUCOSIDASE ACTIVITY

| ACARBOSE CONC. (μg/DU glucoamylase) | INHIBITION (%) GLUCO-AMYLASE[a] | TRANS-GLUCOSIDASE[b] |
|---|---|---|
| 1.25 | 23 | 0 |
| 2.5 | 36 | 0 |
| 5 | 65 | 0 |
| 10 | 86 | 0 |
| 15 | 91 | 0 |
| 20 | 95 | 0 |
| 30 | 97 | 0 |
| 40 | 98 | 0 |
| 50 | 100 | 0 |
| 100 | 100 | 0 |
| 200 | 100 | 0 |
| 300 | 100 | 0 |
| 400 | 100 | 0 |
| 500 | 100 | 0 |
| 600 | 100 | 6 |
| 800 | 100 | 8 |
| 1000 | 100 | 12 |
| 2000 | 100 | 23 |

[a] one unit of glucoamylase was present in the reaction mixture.
[b] 40 units of transglucosidase were present in the reaction mixture.

After inhibition of the glucoamylase in the preparation under test, a substrate known to be susceptible to TG activity is added. In the following general procedure and example, the conversion of maltose into panose, as a function of time, is monitored in order to determine TG activity. As indicated above, other substrates which are acted upon by TG are equally suitable provided a suitable procedure is available for measuring specifically the primary reaction product produced by action of TG on the substrate selected. These substrates include, for example, maltotriose and other oligosacharrides and glycosides containing glycosidic linkages with the α-configurations.

The method of practicing this invention is more fully described by the following general procedure and more specifically by the example.

EXAMPLE OF GENERAL PROCEDURE

Glucoamylase equivalent to 1 to 5 DU is taken in a test tube and diluted to 0.25 ml with (0.02M) acetate buffer, final pH 4.8. Then 0.25 ml of 0.02M acetate buffer containing acarbose is added to give a final concentration of 50 μg acarbose/DU of glucoamylase and the mixture is incubated at 37° C. for 30 minutes. After the specified time, 0.5 ml maltose (20% concentration) in 0.02M acetate buffer, pH 4.8 is added and the mixture incubated for another 60 minutes at 37° C. Enzymatic reaction is terminated by heating the mixture in a boiling water bath for 15 minutes. A blank reaction mixture, serving to correct for any trisacharride contaminant in the substrate, is prepared similarly except that maltose is added after thermal inactivation of the TG. Transglucosidase activity is then measured by determining, using liquid chromatography, the amount of panose formed. A standard curve, made using pure panose is prepared to calibrate the instrument. For glucoamylose samples containing low amounts of TG, a more prolonged incubation period, i.e. 15 to 20 hours, if necessary. The conditions for liquid chromatography were as follows:

| | |
|---|---|
| Column: | HPX-87 (Bio-Rad) |
| Solvent: | HPLC-Grade water |
| Column Temp: | 85° C. |
| Flow Rate: | 1 ml/minute |
| Detection: | Refractive index |

Calculation:
μ mole panose produced/ml of stock enzyme solution =

$$\frac{\Delta \text{ area under panose peak} \times \text{dilution}}{504 \times A}$$

where Δ area under panose peak=(area under panose peak for test mixture)−(area under panose peak for blank mixture). A=slope obtained from panose standard curve; 504=molecular weight of panose.

The method of practicing the invention is further illustrated by the following example.

EXAMPLE

The measurement of TG activity in two commercial samples of glucoamylase, representing products with high TG (I) and low TG (II) levels, is detailed. Samples containing intermediate amounts of TG would be tested after appropriate dilution and a suitable duration of incubation of the acarbose-treated enzyme with maltose selected.

Sample I—The enzyme sample was diluted to 17 DU/ml. To 20 μl of the diluted solution containing 0.34 DU glucoamylase was added 20 μl of a solution of acarbose (concentration 1 mg/ml), this amount of acarbose representing 60 μg/DU glucoamylase. Acetate buffer (0.46 ml, 0.01M, pH 4.8) was then added to give a reaction mixture of total volume 0.5 ml. Maltose (0.5 ml, 20% w/v) was then added and the mixture incubated at 37° C. for 1 hr. Enzyme action was then terminated by heating the reaction mixture at 100° C. for 10–15 min. A control was run similarly but in this case the maltose solution was added after inactivation of transglucosidase by heating.

Sample II—In this case, the enzyme solution (200 DU/ml) was not diluted. To a sample (20 μl containing 4.0 DU) was added 0.24 ml of acarbose solution (1 mg/ml), this amount representing 60 μg acarbose/DU glucoamylase. After addition of 0.24 ml of acetate buffer (0.01M, pH 4.8) to bring the enzyme solution to a volume of 0.5 ml, maltose (0.5 ml, 20% w/v) was added and the mixture incubated at 37° C. for 17 hr. Enzyme activity was then terminated by heating the reaction mixture at 100° C. for 10–15 min. Again a suitable control mixture was included. After termination of enzyme action, measurement of panose and calculation of TG activity is conducted routinely as follows:

High Pressure Liquid Chromatography: A sample (0.2 ml) of the product is diluted to 2.0 ml with distilled water, then filtered through a Millipore filter (0.22 mm) prior to analysis of a 20 μl sample by high pressure liquid chromatography as detailed above. The high pressure liquid chromatography is calibrated by measuring the peak area corresponding to 1 μg of standard sugar (maltose or glucose).

Calculation (illustrated for Sample I): All peak areas are expressed in integrator units and are converted for detector response based on chromatography of a standard sugar.

Corrected area under trisaccharide peak (experimental) = $2.841 \times 10^5$

Corrected area under trisaccharide peak (control) = $0.234 \times 10^5$

Δ Area, trisaccharide peak = $2.607 \times 10^5$

Area under peak for 1 μg standard sugar = $0.059 \times 10^5$ $$\mu g\ panose \equiv 20\ \mu l\ diluted\ sample = \frac{\Delta\ Area,\ trisaccharide\ peak}{Area\ for\ 1\ \mu g\ standard\ sugar}$$

$$= \frac{2.607}{0.059}$$

$$= 44.18$$

So, μg panose in 2.0 ml diluted sample ≡

0.2 ml of incubation mixture = 4418 μg.

Total amount of panose in incubated mixture = amount of panose in 0.2 ml × dilution factor = 4418 × 5 μg = 22090 μg $$\mu mole\ panose\ produced\ by\ 20\ \mu l\ of\ glucoamylase\ solution\ under\ test =$$

$$\frac{\mu g\ panose\ in\ reaction\ mixture}{mol.\ wt.\ of\ panose} = \frac{22090}{504}$$

= 43.83 μmole

μmole panose produced by 1 ml of glucoamylase under test =

2191 μmole

Activity of glucoamylase solution (diluted) = 17 DU/ml

Thus, TG activity = 12888 TG units/100 DU of glucoamylase.

Similar calculations for Sample II show its TG content to be 33 TG units/100 DU of glucoamylase. This determination is also illustrated by the drawing.

What is claimed is:

1. A quantitative method for the determination of transglucosidase activity in glucoamylase preparations which method comprises the steps of:
    (a) providing a culture filtrate on a glucoamylase preparation suspected of having transglucosidase activity;
    (b) adding acarbose as a selective inhibitor to the culture filtrate in an amount of from 50 to 500 μg per DU of glucoamylase to inhibit the glucoamylase activity without inhibiting the transglucosidase activity;
    (c) introducing maltose to the inhibited glucoamylase culture filtrate; and
    (d) determining the transglucosidase activity by measuring, as a function of time, the amount of panose produced.

2. The method of claim 1 wherein the amount of panose produced is measured by liquid chromatography.

3. The method of claim 1 wherein the culture filtrate is obtained from a fermentation broth resulting from the fermentation of *Aspergillus niger*.

4. The method of claim 1 wherein 10% maltose is introduced and the resulting mixture is allowed to incubate at pH 4.8 and 37° C. for 1 hr.

5. A quantitative method for the determination of transglucosidase activity in glucoamylase preparations which method comprises the steps of:
    (a) providing a culture filtrate of a glucoamylase preparation obtained from a fermentation broth resulting from the fermentation of *Aspergillus niger* which filtrate is suspected of having transglucosidase activity;
    (b) adding acarbose to the culture filtrate in an amount of from 50 to 500 μg per DU of glucoamylase to thereby inhibit the glucoamylase;
    (c) introducing maltose to the inhibited glucoamylase culture filtrate; and
    (d) measuring, by liquid chromatography, the amount of panose produced as a function of time and using this measurement to determine the transglucosidase activity.

* * * * *